(12) United States Patent
Schwartz

(10) Patent No.: US 7,596,836 B2
(45) Date of Patent: Oct. 6, 2009

(54) NOSE AND THROAT ANTI-INFLUENZA SOLUTION AND METHOD OF USE

(76) Inventor: Steve W. Schwartz, 3860 Hobcaw Dr., Myrtle Beach, SC (US) 29577

( * ) Notice: Subject to any disclaimer, the term of this patent is extended or adjusted under 35 U.S.C. 154(b) by 0 days.

(21) Appl. No.: 11/799,617

(22) Filed: May 2, 2007

(65) Prior Publication Data

US 2008/0274163 A1  Nov. 6, 2008

(51) Int. Cl.
- *A61K 9/68* (2006.01)
- *A01N 25/00* (2006.01)
- *A61F 13/00* (2006.01)
- *C07D 311/00* (2006.01)
- *C07C 39/06* (2006.01)

(52) U.S. Cl. .................. 24/440; 424/405; 424/434; 549/397; 568/781

(58) Field of Classification Search ............... 424/405; 549/397; 568/781
See application file for complete search history.

(56) References Cited

U.S. PATENT DOCUMENTS

| | | | |
|---|---|---|---|
| 4,066,507 A * | 1/1978 | Takagi et al. ............... 435/71.2 |
| 4,742,046 A * | 5/1988 | Bliah ............................ 514/8 |
| 4,895,727 A | 1/1990 | Allen et al. |
| 6,309,663 B1 | 10/2001 | Patel et al. |
| 6,485,729 B1 | 11/2002 | Smith et al. |
| 6,649,147 B1 | 11/2003 | Ye et al. |
| 7,048,953 B2 | 5/2006 | Vail, III et al. |
| 2001/0049363 A1 | 12/2001 | Rubin et al. |
| 2002/0137724 A1 | 9/2002 | Rubin et al. |
| 2003/0165521 A1 | 9/2003 | Smith et al. |
| 2004/0009245 A1 | 1/2004 | Vail, III et al. |
| 2004/0067203 A1 | 4/2004 | Parikh |
| 2004/0077609 A1 | 4/2004 | Rubin et al. |
| 2004/0241109 A1 | 12/2004 | Parikh |
| 2005/0208083 A1 * | 9/2005 | Annis ............................ 424/400 |
| 2005/0245502 A1 * | 11/2005 | Keller .................... 514/211.07 |
| 2006/0137724 A1 | 6/2006 | Powers et al. |
| 2006/0210482 A1 | 9/2006 | Cassara |

FOREIGN PATENT DOCUMENTS

| | | |
|---|---|---|
| WO | WO 9534276 A1 * | 12/1995 |
| WO | WO 9746205 A2 * | 12/1997 |
| WO | WO 2005049026 A1 * | 6/2005 |

OTHER PUBLICATIONS

Maize Products, 2005, Sorbitol and properties. pp. 1-4.*
Otsuka et al. J. Med. Chemistry. 1994, vol. 37, pp. 4267-4269.*
Kawaoka, Y. New England Journal of Medicine. 2005, vol. 352, No. 25, pp. 2645-2646.*

* cited by examiner

*Primary Examiner*—Sreeni Padmanabhan
*Assistant Examiner*—Samira Jean-Louis

(57) ABSTRACT

A nose and throat anti-influenza solution is described that decreases the likelihood influenza infection and its spread. The solution's components are readily available and have been used to treat humans for other ailments previously, leading to an easily implemented, scalable, safe, and cost-effective solution. The core components of the solution include: specially denatured alcohol (SDA); Triton x-100; sodium saccharin; 1,8 cineole (eucalyptol); thymol; methyl salicylate; menthol; sorbitol and/or glycerin; sodium benzoate; poloxamer 407; polysorbate 80; and distilled water. Optionally, the solution also includes one or more of the following: citric acid; *sambucus nigra* agglutinin; a lectin that binds 2,3 sialic acid; nonoxynol-9; sialyllactose; a protease; a protease inhibitor; and/or chloroquine. The solution is applied to the nasal cavity via a pre-moistened cotton swab or a pre-moistened facial tissue and the solution is applied to the back of the throat via a spray, gum, or gargle solution. Further a nebulizer, atomizer, or inhaler can be used to apply the solution to the back of the throat, to the pharynx, and/or to the respiratory tract.

8 Claims, No Drawings

NOSE AND THROAT ANTI-INFLUENZA SOLUTION AND METHOD OF USE

BACKGROUND OF THE INVENTION

1. Field of the Invention

The present invention relates generally to combating influenza and, more particularly, to using a nose and throat anti-influenza solution to decrease the likelihood influenza infection and its spread.

2. Description of the Prior Art

The common flu is an illness caused by viruses known as influenza. The influenza virus infects the respiratory tract. Compared with most other viral respiratory infections, such as the common cold, influenza (flu) infection often causes a more severe illness. Every year millions of people die from this virus around the world. The virus spreads so easily that tens of millions of people catch it each year. It mutates so fast that no one ever becomes fully immune. New vaccines are needed each year. Even today with all of our advances in medicine and technology and all of our history with this virus there is no known cure. In fact we are not sure how to prevent its spread. The virus has an impact on all aspects of our economy and life.

A new strain of influenza virus known as H5N1, also known as the avian or bird flu has caused growing concerns. The World Health Organization (WHO) is monitoring the virus closely as occurrences of infection continue.

Two differing opinions regarding this strain have been shared since the virus began being reported. Some experts believe it is just a matter of time before an influenza pandemic hits and avian or bird flu (H5N1) may be the strain that causes the pandemic. Some experts believe we are better suited concentrating our efforts on solving current known diseases, other viruses and pandemics. However if it is not H5N1, there will be another influenza strain of utmost concern.

World estimates are that 9 million people will die from this next pandemic. In the United States, the estimates are approximately 500,000 people will die. Based upon the current population census and the mortality rate of the 1918 virus, if the virus hit today we could experience one "silent killer" that creates more deaths in a few short weeks than the annual number of deaths for heart disease, stroke, chronic pulmonary disease, AIDs, Alzheimer's and all cancers combined.

The avian or bird flu is due to an influenza virus. Influenza is defined as:
1. An acute contagious viral infection characterized by inflammation of the respiratory tract and by fever, chills, muscular pain, and prostration. Also called grippe; or
2. Any of various viral infections of domestic animals characterized generally by fever and respiratory involvement.

The influenza virus has two distinct surface proteins called HA or hemagglutinin, and NA or neuraminidase or H and N for short. In addition to coating the virus they provide important functions for infecting the cells and replication. Each virus has exactly one H and one N type of protein. The field of virology has isolated 15 types of the H and 9 types of the N. Each virus is named for the particular type of H and N that it has. For example the Spanish Flu of 1918 was a H1N1 virus. The current avian virus is H5N1. The virus is a member of a family of viruses called the orthomyxoviruses.

The virus is approximately 150 nm long and with a shape that can vary from a spheroid to cylindrical. It has several layers. The outer layer is like a cell wall and is similar to the cell wall of ordinary cells. This is composed of a lipid bilayer membrane with embedded proteins. This offers a general form of protection for the virus. The second layer is felt to be a firmer and hardened shell. It is composed of proteins which are thought to protect the viral RNA genes. Additionally, the proteins in this second layer connect to and integrate with the outer lipid layer.

The virus gains access to a human cell by contact with its surface. The H or hemagglutinin will bind to receptors present on the cell surface. Receptor binding is via multiple low affinity receptors and it is felt that when sufficient binding strength is achieved, the virus enters the cell in a process called endocytosis. The entry vesicle, called an endosome, is transported inside the cell to an area near the nucleus. The virus fuses with the lipid wall of the endosome and eventually, the viral contents including RNA is spilt into the cell cytoplasm. The RNA is transported to the nucleus. The cell is then instructed to follow the instructions in the viral genes. At that point the cell synthesizes more viruses and the viruses then reassemble and are released from the cell in large numbers.

The avian virus has been with the world for quite some time and probably as long as man and bird have been on the planet. Studies of the Avian Flu of 1918 have shown that the virus had an avian origin and this was confirmed in three separate isolates of the virus. One was from a woman frozen on the Alaskan Tundra. There have been four pandemics since 1917 and some have happened despite regular influenza vaccinations of the world populations. Birds like humans can easily pass viruses to each other. In 1997 a strain of virus appeared in the bird population that was particularly deadly. However, the strain was not deadly in ducks, which can carry the virus in their lungs and intestines without symptoms. Because of the deadly nature of the virus and the rapid spread in poultry and wild-birds, the total number of avian virus world-wide is increasing dramatically. It is known that viruses adapt through mutation and recombination, therefore as viral mutations and recombinations continue, the viral strains become more efficient and adaptable. Eventually a human strain that retains the deadly nature of the avian flu (H5N1) will appear. This will likely lead to a pandemic.

Respiratory strains of influenza are the most troublesome because of the high potential for its transmission in mucus and bodily fluids. When people sneeze and/or cough, they are potentially spreading the virus. The virus infects through the respiratory tract, including the nasal cavity and the back of the throat, areas where there are mucous membranes and mucus that can be spread by sneezing and/or coughing.

Typical attempts to fight influenza use vaccines. Unfortunately this does not attack the viruses at their primary entrance and exit from the human body, the nose and throat. Further, new vaccines are needed for new strains of the virus and are not easily scalable. Each year, vaccines are only created for a handful of flu strains, leaving people without comprehensive influenza protection; there would be an estimated six month delay to create a vaccine in response to a pandemic.

Other attempts to fight influenza have used M2 blockers and neuraminidase inhibitors (e.g. Tamiflu® and Relenza®). Unfortunately, flu strains H3N2 and H1N1 in Asia have already shown resistance to M2 blockers. Resistance is also rising against the neuraminidase inhibitors. Additionally neuraminidase inhibitors have other issues such as: limited efficacy; high cost and relatedly, dosage needs are increasing; and side effects such as hysteria and psychiatric symptoms. For instance, consider oseltamivir, a neuraminidase inhibitor. The mortality of oseltamivir treated patients worldwide for the current stain of Avian Influenza H5N1 is close to 50%.

There is evidence from animal studies that the current dosage used to treat influenza and Avian Influenza in particular of 75 mg twice daily is too small and should be increased 2 to 10 fold. In general for ordinary human influenza such as H3N2, treatment must begin within 6 to 24 hours of onset of symptoms in order for it to be effective. There are reports of serious neuropsychiatric symptoms from oseltamivir in Japan including suicide attempts.

Thus, there is a need for a scalable, safe, multi-faceted anti-influenza solution that can be applied topically to the nose, throat, and respiratory tract that has good efficacy against all strains of the virus and that is not easily resisted by future mutations of influenza strains.

SUMMARY OF THE INVENTION

A first aspect of the present invention is to provide an antiviral solution. The antiviral solution includes the following: (a) at least one alcohol; (b) a surfactant; (c) at least one essential oil; (d) at least one hygroscopic substance; (e) a buffered acid; and (f) water.

A second aspect of the present invention is to provide a device for delivering an antiviral solution. The device includes an antiviral solution and an applicator containing the antiviral solution. The antiviral solution includes the following: (a) at least one alcohol; (b) a surfactant; (c) at least one essential oil; (d) at least one hygroscopic substance; (e) a buffered acid; and (f) water.

The present invention is further directed to a method for of preventing or treating a viral infection in a user's body including the following steps: providing an antiviral solution and applying the antiviral solution with an applicator topically to a mucous membrane in a user's body thereby preventing or treating a viral infection in the user's body. The antiviral solution includes the following: (a) at least one alcohol; (b) a surfactant; (c) at least one essential oil; (d) at least one hygroscopic substance; (e) a buffered acid; and (f) water.

Thus, the present invention provides a nose and throat anti-influenza solution that decreases the likelihood influenza infection and its spread. All of the solution's components are readily available and have been used to treat humans for other ailments previously, thereby further providing an easily implemented, scalable, safe, and cost-effective solution.

These and other aspects of the present invention will become apparent to those skilled in the art after a reading of the following description of the preferred embodiment as it supports the claimed invention.

DETAILED DESCRIPTION

In the following description, like reference characters designate like or corresponding parts throughout the several views. Also in the following description, it is to be understood that such terms as "forward," "rearward," "front," "back," "right," "left," "upwardly," "downwardly," and the like are words of convenience and are not to be construed as limiting terms. The description below is for the purpose of describing a preferred embodiment of the invention and is not intended to limit the invention thereto.

The present invention provides for a multi-component solution for attacking the influenza virus and its mechanisms of infection. The solution is intended to be applied topically to an individual's nasal cavity and back of the throat. The individual components and their purposes follow. After describing the various core and optional components and their preferred concentrations, the delivery mechanisms are described. All of the components below are readily available and have been used to treat humans for other ailments previously, leading to an easily implemented, scalable, safe, and cost-effective solution.

Core Solution Components

Preferably, the solution contains the following core ingredients:
  a. Specially denatured alcohol (SDA);
  b. Triton X-100 (4-octylphenol polyethoxylate);
  c. Sodium saccharin;
  d. 1,8 Cineole (Eucalyptol);
  e. Thymol;
  f. Methyl salicylate;
  g. Menthol;
  h. Sorbitol and/or glycerin;
  i. Sodium benzoate;
  j. Poloxamer 407;
  k. Polysorbate 80; and
  l. Water.

Specially Denatured Alcohol (SDA)

Specially denatured alcohol, or SDA, is ethanol that has been specially formulated with other alcohols added to make it unfit for human consumption. Typical additives included methanol, isopropanol, butanol, methyl ethyl ketone, methyl isobutyl ketone, and denatonium. SDA, if consumed directly as a substitute for liquor can cause one to feel nauseous and may cause other physical problems.

In the present invention, SDA was partially chosen in place of using pure ethanol so people will not try to consume the solution to become intoxicated. Generally SDA is viewed as safe for a variety of other medical products that are taken orally; marketed products typically use a concentration ranging from 5-35%. For instance alcohol was used in elixirs, or old-fashioned cough syrups that combine alcohol with a drug (e.g. elixirs contain alcohol concentrations between 3% and 25%, and in various mouthwashes (e.g. Scope contains SDA at a concentration of approximately 8%). Elixirs are described, for example, in "Remington: The Science and Practice of Pharmacy," p. 734, Mack Pub. Co., New Jersey (2000), which is incorporated herein by reference. U.S. Pat. No. 6,641,801 "Gargle method to reduce the duration of common cold symptoms" to Brown postulates administering pure ethanol as a gargle in concentrations between 20 to 95%.

The concentration of SDA in the present invention ranges between 15% and 25%. Preferably the concentration of SDA is 25%. Higher concentrations of SDA are preferable but the concentration needs to be palatable because the final solution of the present invention may be applied to the nose and throat. Also if the SDA concentration is too high, then it may develop a vapor component. Therefore a concentration of between 15% and 25% is an acceptable balance. As mentioned above, there are other types of products (not designed to attack influenza) on the market that use SDA and the range of 15-25% SDA is a reasonable balance between efficacy and safety.

SDA is the preferable alcohol for the present invention because it does contain a variety of other alcohols besides the primary SDA alcohol, ethanol. These other alcohols have the added benefit for providing different alcohol types to affect the influenza virus as described next.

The purposes of SDA in the solution of the present invention are two-fold: 1) SDA helps lyse and puncture holes in the virus's membrane thereby destroying some influenza viruses before they even reach a host cell; and 2) SDA helps change the conformation of hemagglutinin (HA) to render the protein ineffective to infect a host cell; and 3) SDA may change the conformation of hemagglutinin (HA) and neuraminidase (NA) to affect its function.

HA serves two purposes for the influenza virus. First, it helps the virus target host cells by binding to sialic acid-containing receptors on the host cell's surface after which the cell ingests the virus into an endosome via endocytosis. Second, it allows the viral RNA to be introduced into the cell by fusing the virus's membrane with the endosomal membrane. HA begins to accomplish fusion after the host cell begins to acidify the endosome's interior; at an acidic pH (starting at around a pH of 6.0), HA changes its conformation to expose a normally hydrophilic interior portion that can bind with the endosomal membrane. The exposed portion is referred to as a spike and or the HA fusion peptide. Then, as the pH continues to drop, HA continues to refold bringing the viral and endosomal membranes into contact and fusing them together. After fusion has occurred, the virus's RNA is emptied into the cytoplasm after which the cell begins to follow the RNA's instructions and create more viruses: In layman terms, HA acts like a spring-loaded spike that can insert into the endosome's lipid bilayer membrane and pull the two together causing fusion.

The present invention provides for defense against HA's primary mode of action, the unfolding/refolding that takes place in the endosome. HA is normally in a conformation that is not its lowest energy state. SDA may, but also in combination with other solution compound's described below, assist causing HA to change into its lowest energy state which makes the HA ineffective. This conformation change is irreversible. Virgin HA is normally one segment containing disulfide bonds; when cleaved HA becomes two segments (HA1 and HA2) but still is one molecule because of the disulfide bond holding HA1 to HA2. HA needs to be cleaved for the virus to be infectious. Normally, HA enters its lowest energy state after the virus has undergone endocytosis. This lowest energy state is referred to as the fusion conformation. SDA helps HA get to its lowest energy state; SDA is likely helped in this cleaving task by lowering the pH of the present invention's solution as described below (an acidic pH can help cleave HA as well). If the present invention's solution doesn't provide for the cleavage of HA, then the host's body will due to proteases in the respiratory tract, thereby creating an infective HA on the virus. These natural proteases derive from neutrophils, clara cells, macrophages, mucous producing cells, alveolar II cells among others. Further, some proteases are intracellular and others are extracellular.

However, by assisting HA to its lowest energy state before contacting a host cell, the present invention helps render the virus's HA ineffective to either target the sialic acid-containing receptors or to fuse with the endosomal membrane; thereby trapping the virus inside the endosome where it can be digested by the cell's normal pathways. Generally speaking, the present invention provides for HA to be activated or spiked too early and therefore it will not perform its functions correctly and the virus will be unable to replicate in a host cell. The infectivity of the virus is reduced proportionately to the degree of irreversible conformation change of the HA. Therefore there is a target threshold, perhaps at 50%, whereby the virus is rendered ineffective and fusion with the endosomal membrane is prevented.

SDA is the preferred alcohol for causing HA to reach it lowest energy state before the virus meets a host cell. Alternatively, pure ethanol, a tertiary structured alcohol (e.g. isopropanol), or a quaternary structured alcohol (e.g. butanol) could be used in place of SDA. However pure methanol would be undesirable as a substitute for SDA because of the risk of methanol toxicity, which can result in blindness from formaldehyde formed by metabolizing methanol in the body.

Triton X-100

Triton X-100 (4-octylphenol polyethoxylate) is another core component of the solution of the present invention. Triton is a surfactant that helps the solution of the present invention diffuse over the virus membrane and creates interfaces between lipids and water. Triton X-100 (4-octylphenol polyethoxylate) can be used for extracting proteins from lipid membranes. It helps solubilize the proteins by disrupting the lipid bilayer. Thus it can potentiate lysis of the viral membranes in conjunction with SDA or other alcohols and embodied components. In laymen's terms, one theory is that Triton X-100 (4-octylphenol polyethoxylate) may cause the HA to "wobble" more on the viral membrane and increase the probability for the present invention's components to reach the HA-viral membrane interface. This interface is where the components need to reach to lyse the viral membrane and induce the irreversible conformation change to the fusion state conformation.

In the present invention, Triton X-100 (4-octylphenol polyethoxylate) is preferably present at a concentration of between about 0.02% and about 4% by volume. More preferably, Triton X-100 (4-octylphenol polyethoxylate) is present at a concentration of about 1% by volume.

Sodium Saccharin

The solution of the present invention contains a sweetener to make it more palatable with the other components. Preferably, the sweetener is sodium saccharin. In the present invention, sodium saccharin is present at a concentration between 0.1% and 3% by weight.

1,8 Cineole (Eucalyptol)

1,8 cineole or eucalyptol is a core component of the solution of the present invention and is the first of four essential oils in the present invention's solution. The eucalyptus plant and its derived products are generally deemed safe for use in humans. In the present invention, cineole assists a potential host cell defend itself against the virus by integrating with the cell's components and making its defenses more effective. There are several ways that cineole works in the solution of the present invention.

First, 1,8 cineole helps lyse holes in the virus's membrane. The viral membrane is made of the same lipid bilayer membrane as mammalian cells because the virus, when leaving a previous host cell, exits from the cell and takes some of the lipid bilayer with it. Studies on terpenes' (of which 1,8 cineole is one) affect on epidermal bilayer membranes suggest that terpenes disrupt the interlamellar hydrogen-bonding network at the polar head group region. Further, terpenes also appear to increase the hydration levels of the lipid system probably by forming new aqueous channels. See Narishetty S T and Panchagnula R, "Effect of L-menthol and 1,8-cineole on phase behavior and molecular organization of SC lipids and skin permeation of zidovudine." J Control Release. Jan. 20, 2005; 102(1): 59-70.

Second, 1,8 cineole beneficially affects respiratory tract cells. Cineole improves the ciliary mucous transport and mucous clearance in both the nose and the bronchial tree. It also serves as a smooth muscle relaxant to improve airway function and clearance. Further 1,8 cineole has a synergistic affect with SDA. The combination with SDA, and in particular the ethanol in SDA, is cytoprotective. In other words it allows the concentration of ethanol to avoid damaging human cells but not viruses.

1,8 cineole is an essential oil that relaxes bronchial and vascular smooth muscle. It has an effect on the cell membrane to enhance permeability and allow other ingredients to work and can puncture holes and aqueous channels in the virus membrane. The virus cannot repair its outer lipid bilayer membrane whereas a cell can repair its outer lipid bilayer membrane very quickly.

In the present invention, 1,8 cineole is preferably present at a concentration of between about 0.04% to about 0.11% by volume. More preferably, 1,8 cineole is present at about 0.090% by volume. Ideally a high concentration of cineole is desired, but the present invention aims to use safe concentrations for all of its components. Mouthwashes typically use a concentration of 0.092% eucalyptol (1,8 cineole); therefore the preferred concentration, above, was chosen to also contain a similar, safe amount of 1,8 cineole.

Thymol

Thymol is a core component of the present invention and is the second of four essential oils in the solution. Thymol is usually used as an anti-fungal in other products. In the present invention, thymol is primarily present to prevent bacterial and anti-fungal growth in the solution. It also may have ancillary beneficial effects to fight the influenza virus. For example, U.S. Pat. No. 3,632,782 "Thymol as an anti-influenza agent" to Alburn et al described that a dosage of a compound containing 1% to 3% thymol was effective at fighting influenza.

In the present invention, thymol is preferably present at a concentration of between about 0.02% to about 0.10% by volume. More preferably, thymol is present at a concentration of about 0.060% by volume. Other products, such as mouthwashes and dental products use the above preferred concentration as an acceptable amount for preservation purposes and for safety concerns.

Methyl Salicylate

Methyl salicylate is a core component of the present invention and is the third of four essential oils in the solution. Methyl salicylate is also known as oil of wintergreen. In the present invention, methyl salicylate provides antiviral intervention by disrupting a signaling pathway on which the virus relies to exit a host cell after replicating itself. Previous studies have shown that influenza virus misuses the cellular IKK/NF-kappaB signaling pathway for efficient replication and that acetylsalicylic acid (which is similar to methyl salicylate) can inhibit NF-kappaB and subsequently viral reproduction via a mechanism involving impaired expression of proapoptotic factors, subsequent inhibition of caspase activation as well as block of caspase-mediated nuclear export of viral ribonucleoproteins. See Mazur et al, "Acetylsalicylic acid (ASA) blocks influenza virus propagation via its NF-kappaB-inhibiting activity," Cell Microbiol. Feb. 22, 2007; [Epub ahead of print]. The present invention preferably uses methyl salicylate, which is similar to acetylsalicylic acid to produce similar disruptions to the viruses natural replication mechanisms. Methyl salicylate is preferable over acetylsalicylic acid because of the connection between the former and Reyes Syndrome in children. However, alternatively, acetylsalicylic acid could be used in the present invention in place of methyl salicylate.

In the present invention methyl salicylate is preferably present at a concentration of between about 0.03% and about 0.08% by weight. More preferably, methyl salicylate is present at about 0.058% by weight.

Menthol

Menthol is a core component of the present invention and is the fourth of four essential oils in the solution. Menthol is a topical anesthetic and also gives a pleasing odor to the product. It also may have a slight decongestant effect which helps to counter some of the increase in congestion that may result from applying the solution to the nose and throat, as anything foreign to the body may stimulate mucus production. Menthol has been shown to reduce coughing by 50% and may also reduce sneezing. Coughing, and especially sneezing, are the major mechanisms that the influenza viruses use to spread from person to person.

In the present invention menthol is preferably present at a concentration of between about 0.03% and 0.06% by volume. More preferably menthol is present at a concentration of about 0.041% by volume.

Sorbitol and/or Glycerin

The solution of the present invention needs to have enhanced body and texture for application to the nose and throat. Hygroscopic substances perform this function well, as they are molecules with hydrophilic groups that have an affinity to form hydrogen bonds with water molecules and increase the solution's viscosity. Preferably sorbitol and/or glycerin, both hydroscopic substances, are in the solution to provide these features. Alternatively sialyllactose or a dendrimer variant of sialyllactose can be used to enhance the solution's body and texture.

The present invention's body and texture, as used above, can be measured by the solution's viscosity and surface tension. The solution has a viscosity such that it does not dissipate quickly after applying to the nasal cavity and the back of the throat. It needs to stay in place for a sufficient period of time to be effective. For instance, in the nose, it should remain for 5-20 minutes. SDA will have a very low viscosity and sorbitol and/or glycerin or sialyllactose increase the viscosity which allows the solution to remain in the nasal cavity and the back of the throat for a sufficient period of time.

In the present invention sorbitol and/or glycerin is added to the solution to yield a viscosity between that of mucus and normal saline solution. It needs to have a sufficiently low viscosity such that cilia hairs sweep the formation back into the nasal passages, but not too low of a viscosity such that the solution is diluted quickly and looses its potency. Preferably, sorbitol is used alone to accomplish this in solution of the present invention.

Sodium Benzoate

Sodium benzoate is preferably present in the solution of the present invention to serve as a preservative as it is known to prevent the growth of bacteria and fungi. In the present invention sodium benzoate is preferably present at a concentration of between about 0.1 to about 0.2% by weight. More preferably, sodium benzoate is present at about 0.1% by weight. This concentration is generally regarded as safe by the FDA.

Poloxamer 407

Poloxamer 407, a hydrophilic surfactant and solubilizing agent is preferably present in the solution of the present invention to provide additional body and texture. It has a solubility trait such that it acts like a water and lipid solvent at once; this is due to the molecule having both hydrophilic and hydrophobic regions. Poloxamer 407 has thermoreversible properties including thermogelling. It can form micelles at a critical concentration. Poloxamer 407 has mucus like properties including its hygroscopic nature. It is known to adsorb on liposome vesicles. The inventors theorize that poloxamer 407 can adsorb to the surface of the influenza virus lipid bilayer membrane and interfere with binding. It has been shown to increase the half-life of liposomes in solution and does this by causing a degree of stability in the lipid bilayer membrane. The inventors theorize that this stability will reduce fusion potential since one aspect of membrane fusion is to cause temporary instability in both the viral and endosome lipid bilayer membrane.

In the present invention poloxamer 407 is preferably present at a concentration of 20% or less by weight. More preferably, poloxamer 407 is present at a concentration of 5% by weight.

Alternatively, poloxamer 335 or 188 may be used in place of poloxamer 407. Poloxamer 335 and 188 are polymers of varying length containing ethylene-oxide or propylene oxide. Overall, these polymers are relatively long. The triple polymer of ethylene-oxide propylene-oxide and back to ethylene-oxide has repetition of about 100-57-100, respectively (100 ethylene groups connected to 57 propylene groups connected to another 100 ethylene groups all in one chain, all connected together in this order). Therefore, the polymers are about 150 times as long as a standard lipid molecule and approximately 75 times the length (if fully stretched) of a lipid membrane.

Also alternatively, another polymer could be used in place of poloxamer 407 that has sialic acid binding properties. Such polymers include sialyllactose (which is also discussed in more detail below) or polydendritic compounds.

Polysorbate 80

The solution of the present invention may settle into layers while in storage due to the separation of the oils from water. To help prevent this, an emulsifier, or surfactant, is added to the solution. Preferably, polysorbate 80, also commercially known as Tween 80, is used. Alternatively, Polyoxyl 40, Polyoxyl 8, Triton X-100 (4-octylphenol polyethoxylate) (and its variations), sodium lauryl sulfate (SLS), and nonoxynol-9 could be used in place or in combination with polysorbate 80. In addition to its anti-settling effects, polysorbate 80, and if utilized, the alternative emulsifiers or emulsifier combinations, helps to increase the probability that SDA and the other lysing components of the present invention will reach the membrane and lyse the cell. Some of the emulsifiers such as Polyoxyl 40 in addition to inserting into the viral lipid bilayer and contributing to membrane disruption can likely cause steric hindrance. The hindrance is due to the 40 repeat. The selection and concentrations of the emulsifiers are chosen for optimal disruption of the viral membrane, yet protect human cell membranes. Further, the surfactants can be formulated in micelle or non-micelle form depending on concentration and formulation techniques.

In the present invention Polysorbate 80 is preferably present at a concentration between about 1% and about 15% by volume. More preferably, Polysorbate 80 is present at a concentration of about 4% by volume. Alternatively, if sodium lauryl sulfate (SLS) is substituted for polysorbate 80, SLS is preferably present between about 1% and about 5% by volume and more preferably at about 2% by volume.

Water

The components of the present invention are created by adding water until each component is at the appropriate concentration or amount as described herein. Preferably, the water is distilled.

Optional Solution Components

In addition to the above core solution components, the present invention contemplates several additional components that further enhance the solutions anti-viral capabilities. The following additional components are optional and may be added to the solution mix separately or in conjunction with one another.

Lowered pH

Lowering the pH of the present invention's solution is an important optional improvement of the core solution; preferably the solution has a lowered pH for a variety of reasons. The main purpose of making the solution acidic to assist the SDA and other components in the conformation change of HA, as described above. The acidity of the solution changes the charge distribution by increasing the positively charged hydrogen ion density. This causes HA to begin to bend, or fold into the fusion conformation. The solution should remain acidic for a period of time to facilitate the attack on the viruses. Therefore, the acidic solution of the present invention should also be buffered to maximize the exposure time of the virus to the acidic environment created by the solution of the present invention.

A low pH greatly increases the effectiveness of the present invention. Preferably, the solution of the present invention is buffered with a pH between about 3.0 to about 5.0. Preferably, the final pH is about 4.0. To obtain this value, readily available ingredients can be used. Preferably citric acid (sodium citrate) and/or dipicolinic acid are added to the solution to obtain the final pH mentioned above. Alternatively, ascorbic acid (vitamin C) and/or lemon juice can be used to achieve the same effect. The solution is buffered by adding the conjugate base of the weak acids used. For instanced, sodium hydrogen phosphate ($Na_2HPO_4$) may be added to the solution to create a citric acid-phosphate buffer in the solution of the present invention.

Additionally, a zinc chelator can be utilized as an acidification agent. Zinc is needed by the influenza M1 protein and zinc deprivation may change the conformation of the M1 protein. The M1 protein is a matrix protein that provides structural support to the virus's membrane and the influenza virus may become structurally unsound if M1 is compromised by being in a non-optimal conformation. Preferably, the zinc chelator is dipicolinic acid, at a concentration appropriate to provide the above buffered pH ranges and/or value.

Sambucus nigra agglutinin

Sambucus nigra agglutinin, or SNA, is from *sambucus nigrans*, more commonly known as elderberry plants. SNA is a lectin that binds 2,6 sialic acid-containing receptors. The human influenza virus typically binds to 2,6 sialic acid-containing receptors on human host cells. Therefore, this additional optional component helps to prevent infection by viruses that survive the other solution components by coating some of the viruses binding sites on the host cells.

2,6 sialic acid-containing receptors are present in the upper respiratory tracts (e.g. the nasal cavity and back of the throat). These receptors are used for the virus to initially bind to the cell. There are two important isotypes of the receptors; typically human flu virus binds to 2,6 and avain flu virus binds to 2,3 sialic acid-containing receptors. Humans do have 2,3 receptors, they have a higher density of distribution in the lower airways and on ciliated cells in the upper respiratory tract; therefore viruses specific for 2,3 sialic acid-containing receptors that are predominant in the lower airways do not typically initiate the sneeze reflex, which is a terrific mechanism for the influenza virus to spread and increase infectivity. They rather initiate the cough reflex which has less infectious potential than a sneeze. Eventually when the avian flu makes the jump to humans, the viruses mutate to bind to both 2,3 and 2,6 receptors and then eventually the deadly H5N1 virus becomes only bindable to 2,6 sialic acid-containing receptors.

The present invention therefore optionally uses 2,6 sialic acid-containing receptor blockers to help prevent spread through viral binding in the nasal cavity and throat to limit the sneeze transmission of the virus. Preferably, this blocker is SNA at a concentration of 2 µg/mL to 5 µg/mL. Note that the concentration is found by mixing SNA powder at 1 mg/mL and serial diluting it until the solution agglutinates a minimum of 2% a of erythrocytes when incubated at 25 degrees centigrade for one hour in a phosphate saline buffered solution with ph of 7.3.

SNA is derived from elderberry bark and the present invention would not require a high concentration; Sambucol, a product available that uses the lectin SNA would likely 'have a much higher concentration than the present invention due the fact that much of the Sambucol SNA lectin is digested in the GI tract, whereas the solution of the present invention is administered directly to the nasal cavity and the back of the throat, two localized areas where influenza virus initiates infectious contact in people. In addition to deriving SNA from elderberry back, the present invention contemplates deriving a recombinant form of SNA in soybeans to reduce the cost of obtaining the compound.

Sambucol containing SNA taken orally has been shown in several double blind studies to have efficacy against influenza. Sambucol is also claimed to be an immune stimulant. Because of this, the Sambucol is generally not accepted for use in the market for pandemic influenza because of fear of over-stimulating the immune system (through a "cytokine storm"). Though much is known today about the immune response to influenza, the complete picture is not clear especially with respect to causes of the cytokine storm which is a cause of mortality in pandemic influenza. Given the complex interactions with the immune system and fine balance of stimulatory and inhibitor pathways and wide variations in response to different influenza strains no one is in a position to state categorically what the net result of SNA is on the immune system and whether it will help or hurt when utilized against a pandemic influenza strain.

The present invention contemplates that any perceived fears of using SNA is likely avoided if it is only used topically and not administered orally. This is because SNA taken orally will have an affect on the immune system due to binding of SNA to white blood cells. For example, it is unlikely that SNA will be present in para-tracheal lymph nodes. Therefore, in theory, the better approach is to use SNA topically and not orally.

Lectin that Binds 2,3 Sialic Acid-Containing Receptors

The avian influenza virus currently has surface proteins that are specific for 2,3 sialic acid-containing receptors. As noted above, humans do have these receptors in their cells, but usually the 2,3 receptors are located on ciliated cells and those deeper in the respiratory tract as well as the GI tract and not the respiratory tract. However, the avian flu can eventually make the jump to bind to 2,6 sialic acid-containing receptors in the respiratory tract and eventually spread more easily. Therefore the present invention optionally also contains a lectin that binds the 2,3 sialic acid-containing receptors. This will allow the solution of the present invention to attack the avian flu's preferred binding sites.

Lectin is a type of protein that binds to a specific conformation of a carbohydrate chain. Preferably, the solution uses *Maackia amurensis* agglutinin (MAA) as the lectin that binds to the 2,3 receptors. MAA is a lectin that is extracted from the *Maakia amurensis* plant and is used research since it binds strongly to the 2,3 receptors. The preferred concentration of MAA in the solution, if utilized, is between 0.1 mg/mL and 20 mg/mL and preferably at 5 ug/mL.

Alternatively, the 2,3 receptor binding lectin may be one or more of the following (in addition to or in place of MAA), preferred concentration ranges are 0.1 μg/mL to 20 μg/mL unless otherwise specified: *limulus polyphemus* lectin (LPA) from the horseshoe crab (preferably at 5 μg/mL); snail dolabella; slug *limax flavus*; snail *achantina fulica*; oyster *crassostrea gigas*; lobster *homarus americanus*; horshoe crab *tachypleus tridentatus*; horseshoe crab *carcinoscorpius rotunda* (binds both 2,3 and 2,6 sialic acid-containing receptors); wheat germ agglutinin *triticum vulgare* (WGA—binds sialic acid in various linkages); scorpion *masticoproctus giganteus*; spider *aphonopelma cepaeahortensis*; prawn *peneaus monodon*; scorpion *paruroctonus mesaenis*.

Note that the above concentrations are found by mixing a lectin powder at 1 mg/mL and then serial diluting it until the solution agglutinates a minimum of 2% a of erythrocytes when incubated at 25 degrees centigrade for one hour in a phosphate saline buffered solution with ph of 7.3.

Nonoxynol-9

The solution of the present invention optionally also contains nonoxynol-9. Nonoxynol-9 is an emulsifier that helps to inhibit the influenza virus. It binds the virus and has been effective against other lipid enveloped viruses, such as HIV. Generally though, nonoxynol-9 is considered a microcide that can even kill spermatozoa. In the present invention, when present, nonoxynol-9 inserts its hydrophobic moiety into the viral lipid membrane. The hydrophilic portion of the molecule, which is relatively long, interacts with surface proteins. The net effect is disruption of the integrity of the viral membrane. Once inserted into the viral lipid membrane, there may also be possible steric effects from the long hydrophilic portion of the molecule. These steric nature of these interactions could affect the action of the HA and NA on cells.

Nonoxynol-9 should be used at a low concentration to avoid mucus irritation. Therefore, preferably the solution of the present invention optionally contains nonoxynol-9 at a concentration of about 0.05% to about 1% by weight. More preferably, nonoxynol-9 is optionally present at a concentration of 0.05%.

Sialyllactose

The solution of the present invention optionally also contains sialyllactose. Sialyllactose is synthesized from milk and in the present invention is preferably bound to a polymer to create a sialyllactose-containing polymer. The polymer is preferably a polyethylene glycol (PEG) derivative. Alternatively, chitosan could serve as the polymer. It can be thought of as a comb-like substance that helps inhibit the sialic acid-containing receptors from binding to the virus.

Sialyllactose in the present invention can be regarded as a mucin enhancer. Mucin is composed of heavily glycosylated proteins. Normal human respiratory tract mucin has abundant 2,3 sialic acid terminated carbohydrates but relatively little if any 2,6 sialic acid. The mucin bound sialic acid can have a protective effect against influenza by binding influenza hemaglutinin. This serves as a decoy against binding to the sialic acids found in the proteins of the cell membrane. Adding sialyllactose to the solution of the present invention enhances this decoy effect of mucin by introducing additional sialic acid binding sites. Therefore adding sialyllactose to the present invention decreases the probability that the influenza virus will be able to bind to the 2,6 sialic acid-containing receptors and will help prevent infection of a potential host cell.

Preferably, sialyllactose in the solution of the present invention optionally is present at a therapeutically effective concentration. Alternatively, polyglutamic acid (PGA) as well as polyethylenimine dendritic and comb sialic conjugates can be used in place of sialyllactose at therapeutically effective concentrations. Therapeutically effective concentrations can be found by formulating the sialyllactose, PGA, or polyethylenimine dendritic and comb sialic conjugates to have a concentration in the solution of the present invention that protects against 10,000 to 1 billion viruses at 400 HA per molecule. This means that 4 billion to 400 billion per square cm of mucus coverage would preferably be required. In vivo, there is always a flux as cilia sweep the mucus and there is a general clearance mechanism at work. The present invention contemplates that most of the binding happens shortly after-application and disabled virus are swept away by the mucus.

Fundamentally, the sialyllactose assists the mucus.

Protease

The solution of the present invention optionally also contains at least one protease. The protease or proteases cleave HA at its cleavage site between HA's two segments (called HA1 and HA2). The protease is active at approximately pH 4 to pH 5 because if the solution of the present invention uses a lowered pH, as discussed above, then the protease will function at the lowered pH of approximately 4-5 and instantly after cleaving HA into HA1 and HA2, the HA conformation change will take place and the HA spike will be activated early which will help prevent the virus from later breaking out of a host cell's endosome should the virus be taken up into the cell.

There are general proteases in the saliva and even more when neutrophils are present. The proteases naturally present in saliva work at normal pH as expected. The ones released from the neutrophils work at acidic pH levels since they basically are meant to work inside the lysosome that digests endocytosed foreign particle or bacteria. Therefore, there are several proteases that fulfill the above requirements. These are alternative options to use in the solution of the present invention, may be used alone or in combination with other proteases, and include the following: cathepsin B, cathepsin D, cathepsin E, cathepsin G, chymosin, pepsin A, renin, and napsin A. All but cathepsin B above are members of the class of aspartic acid activated proteases called aspartic endopepitdases. Further information on these and other proteases can be found at MEROPS: The Peptidase Database (Rawlings, N. D., Morton, F. R. & Barrett, A. J. (2006) MEROPS: the peptidase database. *Nucleic Acids Res* 34, D270-D272 (available at http://merops.sanger.ac.uk/)). Napsin A was discovered in the human genome project and has since been cloned. It is theorized to be related to immune function.

The preferable protease only acts at an acidic pH range because then the solution of the present invention will induce the HA low energy fusion state conformation. More preferably the protease is active primarily (95% of its activity) at pH of about 5.

Protease Inhibitor

The solution of the present invention optionally also contains a protease inhibitor. This inhibitor needs to be active at a pH of approximately 7 and inactive at a pH of about 5. Normally in the body, at pH 7, if the hemagglutinin (HA) surface molecules on the virus are not cleaved, then natural proteases in the human body will cleave the HA and activate the virus (the HA will not go through the above discussed conformation changes though because of the lack of natural-occurring SDA and/or an acidic environment). The present invention attempts to prevent the natural course of viral infection and force the virus's HA to only be cleaved in the solution's environment which will instantly alter the HA conformation to the lowest energy state (via SDA and optionally the acidic environment). Additionally, in general, the protease inhibitor slows the virus down by inhibiting it from replicating.

When discussing protease and anti-proteases it is important to understand the hemagglutinin cleavage site. The cleavage site is a 19 amino acid sequence that forms a protruding ringed arc on the outside surface of the hemaglutinin trimer. The freshly synthesized hemagglutinin molecule has a cleavage site at position 329 which is normally an arginine amino acid. Arginine is known as a positively charged and hence basic amino acid. There can be a series of basic amino acids in the cleavage sequence. This positively charged sequence of amino acids attracts the protease which cleaves the ringed arc. Normally the arginine at position 329 is lost during this cleavage.

The cleavage sequence can vary with the species of influenza. The sequence has been classified into two basic classes called monobasic and multibasic. The monobasic species usually has a single basic positively charged amino acid such as arginine or lysine. Most influenza A, B and C viruses fall into this class. The multibasic class consists of a cleavage site with multiple basic amino acids with a sequence such as Arginine-xxxxx-Lysine/Arginine-Arginine (referred to as an R-X-K/R-R motif). This multibasic cleavage site is found in influenza A virus subtypes H5 and H7.

The multibasic cleavage site confers an advantage to the virus in that it is more recognizable and hence easier to cleave. It also confers addition virulence in general and allows the virus increase the number of tissues it can invade (tissue tropism).

Also, the monobasic cleavage sites are cleaved by trypsin class proteases. The Multibasic cleavage sites are cleaved by serine subtilizin-like serine type endoproteases. The cleavage of the hemaglutinin can happen at many points during the life cycle of the virus. Cleavage can occur while the hemaglutinin is being formed in the trans-golgi apparatus, after exit from the cell and also after endocytosis but before fusion. When and where cleavage happens depends on the availability of proteases with cleavage capability for the given sequence.

As mentioned above, the ideal protease inhibitor is one that is active at pH 7 (or the normal pH of the tissue that is infected) and inactive at pH of 5 or lower. The inactive pH requirement is not necessary if the protease inhibitor does not interact with the specific proteases included in the solution. The protease inhibitor can work both extracellularly and intracellularly. The lower molecular weight inhibitors are more likely to be effective intracellularly.

There are a variety of endogenous proteases that must be inhibited in the respiratory tract. The proteases are secreted by clara cells, epithelial cells and inflammatory cells such as neutrophils. Proteases are also present from bacteria and even fungi. The ideal protease inhibitor is a cocktail of several inhibitors to cover the spectrum of the types of proteases that might be found. A person who has been treated with strong antibiotics will most likely have few bacteria in the nasal oral pharyngeal cavity but will more likely have an abundance of fungi species such as and *Candida albicans*.

One of the proteins encoded by the influenza virus polymerase acidic (PA) gene has a chymotrypsin protease activity. It has been shown that the virus will not replicate well in the presence of protease inhibitors. In fact, when grown in the lab using the classic MDCK cells, trypsin is usually added along with the cellular support medium otherwise the influenza virus will not replicate very well if at all.

Common proteases found in mammalian cells that the present invention would preferably inhibit include Furin and PC6. These are found in mice, chickens and humans among others. Many mammalian cells additionally have the proteases PC1, PC2, PC3. Proteases in the respiratory tract of humans include tryptase clara, mini-plasmin, ectopic anionic trypsin, mast cell tryptase, tryptase TC30.

The solution of the present invention optionally may use one or more of the below described anti-proteases. Preferably, the diluted concentration of the anti-protease(s) is 1 μM to 50 μM.

Anti-proteases contemplated for inclusion in the solution of the present invention include endogenous antiproteases (or their animal equivalents) such as alpha-2-macroglobulin and surfactant. In addition to an actual protease inhibitor, any compound that stimulated the additional production of a protease inhibitor may be alternatively used in the solution of the present invention. The natural surfactants produced by type II alveolar cells SP_D and SP_A have anti-protease activities.

Further serine protease inhibitors (of which there are over 30 types) may be used. These serpines include alpha1-antitrypsin, EI (Elastin Inhibitor) and TI (Trypsin Inhibitor), DCI, DFP, PMSF, TLCK, TPCK, leupeptin, and Aprotinin Plant anti-proteases that may be used include Soybean Protease Inhibitor, Kunitz soybean trypsin inhibitor (STI), and Lima bean Protease Inhibitor.

Egg White Albumin has abundant protease inhibitors and may be used as an anti-protease source for the solution of the present invention.

Benzamadine is a low molecular weight anti-protease and may be used as an anti-protease for the solution of the present invention.

Cysteine protease inhibitors include E-64, Iodoacetamide, N-ethylmaleimide, cobalt chloride, cadmium acetate, hydroxymercuribenzoate and may be used as an anti-protease for the solution of the present invention.

MetalloProteases include EDTA, EGTA and phenanthroline and may be used as an anti-protease for the solution of the present invention.

DecFAKR-CMD and decrier-CMD which is a peptidyl chloromethylketone are anti-proteases that may be used as anti-protease(s) for the solution of the present invention Peptide aldehydes also can provide some of the functionality of an anti-protease in the solution of the present invention. These are di, tri or tetra peptides where the terminal carboxylic acid is an aldehyde. They penetrate cells well and irreversibly inhibit the reaction. Leupeptin and antipain are some examples of peptide aldehydes contemplated by the present invention. They have a very low toxicity.

Chloromethyl ketones and floromethyl ketones also can provide some of the functionality of an anti-protease in the solution of the present invention. These are a class of short peptides with chloride or fluoride group attached to the carboxylic C terminus.

Boronated acid peptides have very high specificity and also can provide some of the functionality of an anti-protease in the solution of the present invention. These have boron attached to the carboxylic C terminus of short peptide sequences.

Low molecular weight protease inhibitors that may be used in the solution of the present invention that have not been mentioned above include amastatin, antipain, APMSF, Bestatin, chymostatin, and DEP.

Chloroquine

The solution of the present invention optionally also contains chloroquine. Chloroquine is a low dose lysomatrophic agent that helps keep the virus "stuck" in the late endosome and prevent spilling its viral contents into the cell's cytoplasm. In the present invention chloroquine basically affects the endosome by preventing the inner-endosomal environment from becoming acidic. Chloroquine prevents this by keeping the inner-endosomal environment at approximately pH 6 or higher. Because HA needs a pH of approximately 5, chloroquine helps prevent HA from spiking and facilitating the fusion of the viral membrane to the endosomal membrane; thereby keeping the virus stuck within the endosome where the cell's natural defenses can then have sufficient time to destroy the virus.

Chloroquine accomplishes this endosomal pH regulation likely due to the substances similarities with proton pump inhibitors. The endosome is made more acidic (pH of about 5) when proton pumps increase the $H^+$ concentration inside it. Therefore chloroquine inhibits proton pumps from functioning properly and prevents the inner-endosomal environment from dropping to a pH low enough (approximately pH 5) to cause HA to go through its conformation changes as detailed above.

Preferably chloroquine is optionally present at a preferred concentration of 0.5 µM to 100 µM and more preferably 10-28 µM. This is a concentration higher than a dosage that one would take orally to treat other ailments such as malaria. The solution of the present invention can have the higher concentration of chloroquine because it is not consumed, but only applied topically to mucous membranes, preferably in the nasal cavity and the back of the throat.

Another reason that it is beneficial to provide topical application of chloroquine is related to its beneficial affects on the immune system to help fight an influenza viral infection. It enhances the dendritic cell (DC) cross antigen presentation. This activates MHC I antigens. This is the preferred immune response because it immediately activates CD8+ T cells. These are cells that become killer T cells and they will find respiratory epithelial cells that have been infected and immediately kill (with an apoptotic effect) using granzymes and or cytokines thus preventing further spread and replication of the virus. The DC cells take soluble antigens from the virus, digest them, and present them to CD8++. For influenza this is a critical response of the adaptive immune system. This response is also the one that is activated fairly quickly in the first 1-5 days of an infection. Also the cross presentation may stimulate memory T cells (from previous influenza infections) and mobilize these quicker.

Chloroquine has also been reported to affect antigen presentation of class MHC II antigens. It is possible that this could hamper an immune response. This process generally takes place in the lymph nodes and therefore by giving it topically rather than systemically the MHC II antigen presentation should proceed normally. This is beneficial because some individuals will need the TH2 immune response. In this manner chloroquine given topically enhances TH1 response and TH2 response.

Chloroquine dosage example: A treatment dose of chloroquine (from a recent HIV treatment trial) is 250 mg of chloroquine phosphate twice daily. This is a dosage level that must be monitored closely due to toxicity of oral chloroquine which is well known. This includes ocular complications and renal toxicity. A dose often used for prevention is 300 mg once per week. The serum half-life is 4 days. Chloroquine has been shown to be effective against HIV in clinical trials. However, the response is directly related to the dosage given.

The molecular weight of chloroquine phosphate is 515.92 g/mol. Determination of the amount of chloroquine needed to deliver an effective dose to the respiratory epithelium can be found as follows. Assuming a desired tissue level to inhibit chloroquine is 27.1 µM, and that this can be achieved with 5 mL diluted solution, the dosage needed is 7 mg of chloroquine. Even if this were used four times daily for a total of 20 mL this would be only 28 mg of chloroquine which represents a very safe level and one that would not require systemic monitoring. If instead 10 mL was used, this would still be 48 mg which is a safe amount of chloroquine. The benefits of avoiding renal and ocular toxicity are clear.

Delivery Mechanisms

The solution of the present invention is prepared by combining the core components and any desired optional components as discussed above. After preparing the solution, delivering the anti-influenza solution to the mucous membranes of the nasal cavity and back of the throat is accomplished through several different delivery mechanisms. Preferably, the solution or two formulations contemplated by the present invention are applied at approximately the same time (within 20 minutes) to both the nasal cavity and the back of the throat. More preferably, and especially during an infection, the solution or two formulations contemplated by the present invention are applied within 5 minutes to both the nasal cavity and the back of the throat. The goal of the following delivery forms is to attempt to disseminate the solution to as many people as possible, especially those who may already be infected.

First, the solution of the present invention may be applied to the nasal cavity through either a pre-moistened swab or a pre-moistened facial tissue, both impregnated with the solution. Preferably, solution is delivered to the nasal cavity via the pre-moistened swab, which is preferably a soft, prepackaged cotton swab, contained in a sealed package. Alternatively, a commercially available cotton swab, such as a Q-Tip swab may be used and dipped in a vial of the solution immediately before applying to the nasal cavity. The key is that one may use the pre-moistened swab to apply the solution to the back of the nasal cavity so it is present where the influenza virus exists or begins an infection.

A pre-moistened facial tissue may be utilized to apply the solution to the nasal cavity. The benefit of using a pre-moistened facial tissue is that these could be used by people sneezing, who may already be carrying the influenza virus. Therefore providing the solution in a pre-moistened tissue may facilitate greater use of the solution in an already potentially infected segment of the population; further the pre-moistened tissue may be prepackaged and contained in a sealed package. However there still is a need to apply the solution to the back of the nasal cavity and a pre-moistened tissue would have to be used in a special manner to accomplish this goal. The tissue may be rolled into a cylindrical-like shape and inserted into the nose before and/or after sneezing to apply the solution to the back of the nasal cavity. Preferably, the rolled tissue is inserted into the nose immediately after a person sneezes to treat a potential influenza infection. After inserting the rolled tissue into the nose, the rolled tissue should be squeeze so the solution is pushed out onto the nasal mucosa.

Second, the solution of the present invention may be applied to the back of the throat via a spray bottle, gum, or gargled solution (contained in a bottle). Further, the solution may be alternatively delivered via a nebulizer, atomizer, or inhaler; this would allow the solution to be applied to the back of the throat, to the pharynx, and/or to the respiratory tract. Preferably, the solution is delivered to the throat by a gargled solution because gargling the solution offers the most consistent and largest surface area coverage. Again, the key is to apply the solution to the back of the throat and not just swish the solution inside the mouth or front of the throat.

It is important to apply the solution to both the nasal cavity and the back of the throat as, surprisingly, the viral infection can move from the nose to the throat and vice versa. If only the nasal cavity or the back of the throat are covered with the solution of the present invention, then the virus can generally move to the other location within 6-12 hours.

Certain modifications and improvements will occur to those skilled in the art upon a reading of the foregoing description. By way of example, the solution may be delivered to the nasal cavity with a spray bottle, mister, nebulizer, atomizer, or inhaler. Also, the applicator may be the same form factor for application to both the nasal cavity and the back of the throat; e.g., a spray bottle or mister may be utilized with a solution contemplated by the present invention and the spray bottle could be designed and used to apply the solution to both the nasal cavity and the back of the throat. Additionally, formulation substitutions that are recognized in the art could be implemented for some of the ingredients. Further, the solution may be formulated to be applied to the entire respiratory tract, including alveoli. The above mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the following claims.

What is claimed is:

1. An antiviral solution comprising:
   a) 15-25% Specially Denatured Alcohol (SDA);
   b) between about 0.02% and about 4% 4-octylphenol polyethoxylate by volume;
   c) between about 0.04% to about 0.11% 1,8 cineole by volume;
   d) between about 0.03% and 0.06% menthol by volume;
   e) between about 0.02% to about 0.10% thymol by volume;
   f) between about 0.03% and about 0.08% methyl salicylate by weight;
   g) sorbitol and/or glycerin to increase the viscosity and add body and texture so that a sufficient amount of solution remains in the nose and throat for 5-20 minutes after application;
   h) citric acid as a buffering agent for achieving a pH between 3.0 and 5.0;
   i) and water (q.s. to 100%).

2. The antiviral solution of claim 1, further comprising dipicolinic acid useful as an acid and a zinc chelator for citric acid in order to create a buffered solution with a pH range of 3.3 to 4.2.

3. The antiviral solution of claim 1 or claim 2, further comprising *Sambucus Nigra* agglutinin.

4. The antiviral solution of claim 2, further comprising cathepsin B that is active at about pH 4 to about pH 5 and leupeptin that is active at about pH 7 and inactive at about pH 4 to about pH 5.

5. The antiviral solution of claim 1, further comprising chloroquine.

6. The antiviral solution of claim 2, further comprising chloroquine.

7. The antiviral solution of claim 3, further comprising chloroquine.

8. The antiviral solution of claim 4, further comprising chloroquine.

* * * * *